United States Patent
Drake (10) Patent No.: US 11,027,041 B2
(45) Date of Patent: Jun. 8, 2021

(54) STABLE AND ROBUST BLENDED HEMOSTATIC COMPOSITION

(71) Applicant: James Drake, Minnespolis, MN (US)

(72) Inventor: James Drake, Minnespolis, MN (US)

(*) Notice: Subject to any disclaimer, the term of this patent is extended or adjusted under 35 U.S.C. 154(b) by 29 days.

(21) Appl. No.: 16/458,134

(22) Filed: Jun. 30, 2019

(65) Prior Publication Data
US 2020/0405907 A1  Dec. 31, 2020

(51) Int. Cl.
A61L 24/00 (2006.01)
A61L 24/10 (2006.01)
A61L 15/12 (2006.01)
C08L 89/04 (2006.01)
C08L 3/04 (2006.01)

(52) U.S. Cl.
CPC ....... *A61L 24/0094* (2013.01); *A61L 2400/04* (2013.01)

(58) Field of Classification Search
None
See application file for complete search history.

(56) References Cited

U.S. PATENT DOCUMENTS 8,575,132 B2 * 11/2013 Ji ................ A61L 24/0036
514/60
2016/0166655 A1 * 6/2016 Gagnieu ............ A61P 7/04
424/489

* cited by examiner

*Primary Examiner* — Kyung S Chang
(74) *Attorney, Agent, or Firm* — Mark A. Litman & Associates, P.A.

(57) ABSTRACT

A hemostatic composition of matter includes a coherent blend of collagen fibrils combined with starch particles as a fluffy mass with hemostatic properties better than collagen fibrils alone or starch particles alone, the composition exhibiting a level of coherence wherein the composition can be lifted, without crushing fibrils, without loss of more than 5% of 10% of a total weight of starch particles from the composition. Sheets with less than 10% by weight of additional binder are also disclosed.

9 Claims, 3 Drawing Sheets

Electron Micrograph showing a Mixture of 53% Starch Micro Particles and 47% Collagen micro fibrils.

Figure 1. Electron Micrograph showing a Mixture of 53% Starch Micro Particles and 47% Collagen micro fibrils.

Figure 2. Electron Micrograph showing a Mixture of 76% Starch Micro Particles and 24% Collagen micro fibrils.

Figure 3. Electron Micrograph showing a mixture of 55% Modified Starch Particles (Responder®, Starch Medical, Inc) and 45% Collagen micro fibrils (Avitene®).

STABLE AND ROBUST BLENDED HEMOSTATIC COMPOSITION

RELATED APPLICATION DATA

This Application claims priority from Provisional U.S. Patent Application Ser. No. 62/728,856, filed 9 Sep. 2018 and titled "STABLE AND ROBUST BLENDED HEMOSTATIC COMPOSITION."

BACKGROUND OF THE INVENTION

1. Field of the Invention

The present invention relates to the field of wound management and particularly to the field of wound management with hemostatic devices and compositions.

2. Background of the Art

When mammals receive injuries that result in bleeding from tissue, the bleeding is countered by an elaborate cascade of biochemical reactions that attempt to close off damaged vessels to prevent further blood loss. Both cellular elements (platelets) and proteins (clotting factors) participate in this process. This process to control bleeding is termed hemostasis.

Blood vessels are strengthened by an outer smooth muscle layer containing the protein collagen. The collagen layer is normally shielded from the blood by the endothelial cells lining the vessel. As blood flows from the damaged vessel, two blood components, von Willebrand Factor and platelets, attach to the outer, normally shielded layers of collagen in the walls of the damaged vessel to form an initial plug. Upon binding to collagen, platelets become activated and release numerous biochemical factors that activate the protein-mediated side of the hemostatic system. This process ultimately results in the conversion of inactive prothrombin into active thrombin. Thrombin is the catalyst for the polymerization of fibrinogen (a soluble, circulating protein) into insoluble fibrin. Fibrin adheres to and strengthens the platelet plug. This fibrin/platelet clot stabilizes the initial platelet plug and forms a barrier to further blood loss.

The formation and dissolution of blood clots is controlled by a complex system of positive and negative feedback loops that prevent blood loss by initiating clotting and also prevent clotting from becoming pathologic. A number of factors can interfere with hemostasis. Severe trauma may present a situation where blood flow is simply too excessive for the initial platelet plug to form. Deficiencies in the hemostatic system caused by genetic or health issues can result in diminished clotting. Drugs such as thrombin inhibitors like heparin or platelet inhibitors such as aspirin or Plavix given to prevent formation of internal clots can result in impaired hemostasis.

Hemostatic devices and compositions have been created to artificially enhance or initiate the clotting process independently or in combination with mammals' natural clotting process. Numerous types of devices have been described in the art to facilitate hemostasis:

1. Products containing blood clotting components such as thrombin and/or fibrinogen. Examples of such products are Tisseel (Baxter), or Thrombin (Lee Biochemical, King Pharmaceutical). These agents act to increase the production of fibrin at the wound site.
2. Styptics such as aluminum chloride or potassium ferrate which coagulate blood proteins and constrict injured vessels. They are primarily useful for controlling minor bleeding.
3. Tamponade-based products, such as gauze or Gel Foam (Pfizer, Inc). These products attempt to stem blood flow by physically impeding flow from the injured vessels.
4. Mixed effect products that try to create tamponade and accelerate clotting. Positively charged polymers such as chitosan fibers (SoftSeal hemostatic pads, Chitogen Inc) or flakes (Celox, MedTrade Products, Ltd) attach to negative charges on tissue, platelets and red blood cells to create tamponade as well as activate platelets. Chitosan is derived from chitin, a natural product found in crustacean shells, fungi and insects. U.S. Pat. No. 8,703,176 (Zhu, et al) describes chitosan fibers treated and formed as hemostatic agents. Non-woven fabrics and fleece comprised of chitosan fibers are treated with organic acids to enhance tissue adhesion and hemostatic efficacy. The treated chitosan is combined with starch microspheres to produce a hemostatic device with good efficacy.

Collagen fibrils (Avitene®, Davol, Inc, and Instat®, Ethicon, Inc.) as disclosed in U.S. Pat. No. 6,361,551 (Torgerson) and U.S. Pat. No. 3,742,955 (Battista) are useful as tamponade agents and also contain sites that interact with platelets to enhance clotting. The Battista patent discloses collagen particles (e.g., fibrils) of the fiber that have a hemostatic activity. Torgerson shows fibers and fabrics that are equivalent to the hemostatic activity of the collagen particles from which the fiber is formed. The collagen fibers of the invention and hemostatic fabrics formed thereof optionally include hemostatic agents and/or other therapeutic agents, to further promote hemostasis and wound healing. The Torgerson Patent evidences exemplary hemostatic agents as including a thrombin molecule, a fibrinogen molecule, a source of calcium ions, an RGD peptide, protamine sulfate, epsilon amino caproic acid, and chitin. In the preferred embodiments, the hemostatic agent is thrombin. The hemostatic agents can be introduced into the hemostatic devices at any stage during the preparation of these devices. Modallo (U.S. Pat. No. 6,454,787) describes foams and sponges fabricated by freeze drying suspensions of collagen fibrils 5. Micro porous particles such as Arista® (Davol, Inc), QuikClot™ (Z Medica) or modified starch particles (Responder®, Starch Medical Inc) described in U.S. Pat. No. 8,575,132 (Ji). These products have strong hemostatic effects. The particles rapidly imbibe water from the blood and concentrate the larger blood elements such as proteins, platelets, and red blood cells on the surface of the particle. The concentrated blood components create a thick gel that impedes blood loss. Platelets immobilized in the gel are also activated and accelerate clotting. Combinations of some hemostatic agents have been used in attempts to secure synergistic effects. Gelatin sponges soaked with a solution of thrombin are widely used to tamponade a wound and hopefully accelerate fibrin formation through the added thrombin. U.S. Pat. No. 8,703,176 (Zhu, et al) describes hemostatic devices combining chitosan fibers with micro porous starch particles to achieve good hemostatic properties.

In seeking improved hemostatic devices, those skilled in the art may be motivated to try combinations of hemostatic agents, thereby hoping, without specific expectations of results, to achieve greater hemostatic efficacy through synergistic effects. It is generally thought that to achieve a useful synergistic effect, each partner should operate by a different hemostatic mechanism. Thus the combination of gel foam and thrombin hopes that the tamponade effect of the gel foam and the increased production of fibrin by thrombin will achieve a greater effect than either product alone. Similarly, for increased hemostatic result, the combination of chitosan with starch particles as shown in U.S. Pat. No. 8,703,176 relies on the ionic attraction between positively charged chitosan with negatively charged cellular and tissue components combined with the concentration and platelet activation effects of starch particles.

One such combination that may be useful to try would be mixing collagen micro fibrils, such as Avitene® or Instat®, with starch particles, such as Arista® or Responder®. Both collagen micro fibrils and the starch particles have good hemostatic properties and each operates by a different mechanism. Seeking to examine such a combination for symbiotic hemostatic effects, mixtures of the collagen and starch particles were prepared with surprising results. The combinations exhibited new and unusual properties that are herein described.

SUMMARY OF THE INVENTION

A hemostatic composition of matter includes a coherent blend of collagen fibrils combined with starch particles as a fluffy mass with hemostatic properties better than collagen fibrils alone and starch particles alone, the composition exhibiting a level of coherence wherein the composition can be lifted, without crushing fibrils and preferably without loss of more than 5% or more than 10% of a total weight of starch particles from the composition. Sheets with less than 10% by weight of additional binder are also disclosed.

DETAILED DESCRIPTION OF THE INVENTION

A composition of matter can include a coherent blend of collagen fibrils combined with starch particles as a fluffy mass with hemostatic properties better than collagen fibrils alone and starch particles alone, the composition exhibiting a level of coherence wherein the composition can be lifted, without crushing fibrils, without loss of more than 5% or more than 10% of a total weight of starch particles from the composition. (In determining total weight, moisture content is not considered in the total weight calculation and should be deducted from the solids' total weight.) The composition may have the collagen fibrils with an average length of less than 1000 µm (and more than 5 µm). The composition may have the starch particles with an average diameter of less than 1000 µm (and more than 2 µm). A method of forming the coherent and stable composition of matter which is a coherent blend of collagen fibrils combined with starch particles as a fluffy mass with hemostatic properties can be performed by physically admixing collagen fibrils and starch particles together in a weight ratio of from 2% to 95% by total weight of the composition as collagen fibrils and from 98% to 5% by total weight of starch particles. The admixing may be performed for at least 15 seconds with a force that is insufficient to reduce the average collagen fibrils length by more than 10%.

The composition may be provided as a flexible sheet of material of the coherent blend of collagen fibrils combined with starch particles by adding no than 10% by total weight of the flexible sheet as an adhesive maintaining sheet shape of the composition. The sheets may be made with less than 3% by total weight of the sheet additional adhesive (material other than the starch, modified starch and collagen), and may, in fact, be made with 0% additional binder. This can be accomplished by compaction of the materials (e.g., in a paper pressing apparatus, using the natural adhesive properties of the starch (or modified starch) particles and collagen. Pressure under high humidity conditions may assist in assuring an adhesive effect of the materials, either by light solubilization of materials or activation of ionic species, causing an attraction between different components.

According to the Battista Patent (supra), a finely-divided fibrous collagen and fibrous product derived from collagen which is useful hemostatic agents and have unique adhesive properties in contact with a severed biological surface in a warm blooded animal when wet with blood.

The composition of matter of the fibrous collagen particle may include finely-divided fibrous collagen products having a surface area of at least 1 square meter per gram, preferably from about 15 to about 30 square meters per gram, and a bulk density of not more than about 8 pounds per cubic foot, preferably between about 1.5 and 6.0 pounds per cubic foot. The preferred fibrous collagen products are partial, ionizable acid salts of collagen containing from about 50 to 90 percent of the theoretical stoichiometric bound acid content.

The surface area is determined by the conventional nitrogen adsorption method using the Perkin-Elmer Sorptometer. The bulk density is determined by adding the fibrous product to a container of known volume without compression and weighing the amount of added material. The fibrous collagen products having the foregoing characteristics possess unique adhesive properties when wet with blood, and these adhesive characteristics are demonstrated in surgical experiments with animals. Fibrous collagen products outside the scope of the products of the present invention do not exhibit the unique adhesive properties.

The fibrous collagen products may be prepared by mechanically dicing or chopping wet, undenatured collagen or delimed edible collagen, fiberizing the diced or chopped collagen, mechanically dispersing the collagen fibers in an aqueous liquid which controls the swelling of the collagen fibers, replacing the bulk of the water associated with the fibers by a water-miscible organic liquid, drying the fibrous collagen product and finally deaggregating the collagen fibrils or fluffing the dried product. Alternatively, the wet undenatured collagen or delimed collagen is mechanically diced or chopped, treated with a water-miscible organic liquid to remove the bulk of the water, dried, and then subjected to the final deaggregating or fluffing operation.

The wet collagen such as hide may be diced or chopped into small fragments of from one-fourth to one-half inch sizes in a cutting or grinding mill, such as, for example, an Urschel Mill. These fragments may be mixed with crushed ice and then passed through the Urschel Mill with cutting heads of smaller dimension to fiberize the collagen into a coarse fibrous product.

If swelling or hydration of the collagen fibers is not controlled during the subsequent treatment wherein the collagen is subjected to mechanical shredding or opening in a liquid medium, excessive hydrogen bonding or densification will occur when the material is dried down, thereby effectively preventing the satisfactory deaggregation of the collagen fibrils during the final mechanical treatment. The initial swelling of the collagen fibers in the wet state affords many more sites for hydrogen bonding than is desirable, thus leading to a dried material which may be hornified and difficult to deaggregate into the constituent fibrils or "fluff." When hornification and densification occur, the product will not have the physical characteristics required to provide the desired adhesion to severed biological surfaces in warm-blooded animals that are wet with blood nor will it provide the required mechanical properties of the collagen-blood matrix between the severed surfaces.

The terminology "mechanical properties of the collagen blood matrix" is used to designate the property of a mixture of the fibrous collagen product and blood that holds together the mixture sufficiently and has sufficient tensile strength to resist separation of the fibers and thereby seal the wound. The in vitro test procedure to be described is a direct measure of this mechanical property.

The wet or moist fibrous collagen is mechanically opened and the fibers dispersed in an aqueous liquid, which controls the swelling of the fibers. The aqueous liquid comprises water and a water-miscible organic liquid such as low molecular weight alcohols, acetone, and the like. The liquid may comprise the organic liquid such as methanol, ethanol, isopropanol, methylethylketone, acetone and the like and water in a weight range of from about 90 percent of the organic liquid to 10 percent water to about 50 percent organic liquid to 50 percent water, preferably 75 percent organic liquid and 25 percent water. Where the proportion of water is too high, the collagen fibers swell to such a great extent that a larger number of sites are provided for hydrogen bonding and attendant densification during the subsequent drying step. When this occurs, excessive hornification and/or densification occurs and it becomes commercially unfeasible to subsequently deaggregate or fluff the fibrous product and attain the bulk density and the surface area requirements necessary for the present invention. Although such product will possess some hemostatic properties, it does not possess the desired adhesion to severed biological surfaces and will not provide the required mechanical properties of the collagen-blood matrix between the severed surfaces.

The bulk of the liquid is drained from the mass and the fibrous collagen slurried and washed with a water-miscible organic liquid such as the alcohol or acetone and again the bulk of the liquid is separated from the partially swollen wet fibers. Preferably, the fibrous material is slurred in the organic liquid to reduce the water content to a minimum. In general, the use of three slurrying steps with the organic liquid will reduce the amount of water present to about 1 percent. The organic liquid is removed as by centrifugation and final drying. Drying may be effected either by oven drying or vacuum drying as at, for example, 40° C. under a 29 inch vacuum for about 16 hours. In general, this vacuum drying will reduce the volatile content to under 1 percent.

Before the final deaggregation into constituent fibers or fluffing operation to produce the product having the required surface area and bulk density, the fibrous material is preferably conditioned to contain about 8 to 15 percent volatiles such as water and/or organic liquid. This conditioning may be readily effected by allowing the product to remain at normal atmospheric temperatures and humidities for from about 8 to 24 hours. The final fiber deaggregation or fluffing operation is necessary to provide the requisite bulk density and surface area. This operation is, in effect, an "opening" operation which is somewhat comparable to the deaggregation of chrysotile fibrils. In this art, this opening separates some fiber bundles into their ultimate individual chrysotile fibrils. In forming the product of the present invention, the final fiber deaggregation or fluffing operation does not separate all of the dried bundles into ultimate individual fibrils but the product does contain finer fiber bundles (smaller in diameter) as compared to the coarser fiber bundles obtained at the end of the drying and conditioning operations. This deaggregation or fluffing may be accomplished by apparatus such as a Waring Blender or, preferably, a hammer mill type comminution mill such as a Fitz Mill.

Where it is desired to produce a partial salt of collagen, the required amount of an ionizable acid may be incorporated in the aqueous liquid wherein the fibrous collagen is dispersed. The amount of acid incorporated in the aqueous liquid is such as to provide the product with a bound acid content of from about 50 to 90 percent preferably about 60 percent of the theoretical stoichiometric bound acid content. After the acid has reacted with the dispersed collagen, the reaction mass is subjected to slurrying and washing with the water-miscible organic liquid and the collagen salt processed as above described.

Alternatively, the partial ionizable salt of collagen may be prepared as described in U.S. Pat. No. 3,628,974. In accordance with the method described in that application, diced or chopped undenatured collagen is introduced into and mixed in a water solution of an ionizable acid, the pH of the solution being between about 1.6 and about 2.6 based upon a 1 percent by weight solids content of the mixture. The mixture is agitated to permit the desired reaction between the collagen and acid and produce a partial salt of collagen containing between about 50 percent and 90 percent of the theoretical stoichiometric bound acid content.

After separating the reacted collagen from the bulk of the solution and washing it, the fibrous product may be recovered by drying. Because of the use of the aqueous liquids, hydrogen bonding occurs and the product is hornified to some extent. A product satisfactory for the present invention may be obtained by a severe deaggregation procedure and fluffing operation. For example, a fibrous product prepared in this manner will require a minimum of two passes through a hammer mill such as a Fitz Mill in order to provide the requisite bulk density and surface area.

Although the partial salt of collagen may be prepared by the use of the water-acid solution in a manner as described, the partial salt after its formation and recovery in a wet state may be slurried and washed several times with a water-miscible organic liquid as described above and then dried. Such product will be less hornified than that dried directly from the water system. In general, such product requires only two passes through a Fitz Mill to produce a final product having the required bulk density and surface area.

Alternatively, the wet collagen source material is diced or chopped into small fragments and then introduced into and mixed in a water-miscible organic liquid such as ethanol or isopropanol. Mixing is continued for about one hour so as to permit thorough penetration of the organic liquid into the small fragments. The bulk of the liquid is then separated as by draining or centrifuging and the recovered fragments again introduced into and mixed in the organic liquid for about 1 hour. Again, the bulk of the liquid is separated and the procedure repeated. At the end of this period, the liquid is centrifuged from the mixture and the wet fragments dried as by oven drying or vacuum drying. The resulting product, after conditioning as described above, is then subjected to a fiberizing and deaggregation or fluffing operation. If it is desired to produce a partial ionizable salt of collagen, the desired amount of acid may be mixed with the organic liquid in any one of the above described steps. In such instances, the time of treatment with the organic liquid containing the acid should be prolonged to permit the required reaction between the acid and the collagen. Obviously, the time periods may be reduced by operating under pressure.

The foregoing discussion describes, in general, the preparation of products under conditions wherein the pH of the treating solution is neutral or below pH 7. Products having the required bulk density, surface area and adhesive characteristics may also be prepared wherein the treating solution is on the alkaline side that is, at a pH above 7. Thus, products with the required properties have been prepared by substituting an alkali such as sodium hydroxide, potassium hydroxide and ammonium hydroxide for the acid of the treating solutions. These treating solutions had a pH of approximately 9. The processing procedures are identical to those described hereinabove.

The suitability of the collagen product for its intended uses may be determined by a relatively simple laboratory in vitro procedure which has been termed a "HAT Test" or "Hemostat-Adhesive Test." In this procedure, a cone penetration test is performed utilizing a Penetrometer such as used in the testing of lubricating greases and bituminous materials in accordance with ASTM D 217-67 T. In this test, 1.2 grams of the fibrous collagen product is mixed with 3.5 milliliters of outdated human blood, that is, between 21 and 31 days after it was drawn and stabilized with standard citrate solutions in accordance with normal procedures.

Hemostatic micro porous starch particles as described in U.S. Pat. No. 6,060,461 (Drake) and Roberts (U.S. Pat. No. 9,649,482) or the modified starch particles shown by Ji (U.S. Pat. No. 8,575,132) provide the second component of the discovery. The micro porous particles of Drake are formed by an emulsion polymerization process. Starch is suspended in water and the suspension is dispersed with vigorous mixing into an organic solvent such as toluene to form a water-in-oil emulsion. The drop size of the starch solution is controlled by varying the shear rate of mixing of the emulsion. Once droplets of the proper size range are obtained, a cross linking agent, such as epichlorohydrin, is added. The cross linking agent ties the starch molecules in each droplet into a continuous three dimensional network of intertwined starch polymer chains. Once the cross linking is complete, the emulsion is broken by the addition of water soluble alcohols and the starch particles are further washed to remove water and toluene, followed by vacuum or freeze drying. The resulting spherical starch particles have a micro porous structure and rapidly swell when exposed to water or blood. The cross linked starch particles cannot fully separate when wetted, but each particle will swell to a size limited by the degree of cross linking. The swollen starch particles have a porous structure that excludes large molecules, red blood cells and platelets.

As discussed earlier, the mode of action of the micro porous particles is due to the rapid absorption of water from the blood. Upon contact with blood, water rushes into the particle, and blood components are trapped on the surface of the particle and rapidly form a thick, viscous gel. The thick gel of starch particles and blood components adheres to the tissue, seals severed blood vessels, and acts to prevent further blood loss. Platelets trapped in the gel are activated by shear forces created by the flow of water past the immobilized platelets and initiate the formation of fibrin which further strengthens the clot. The micro porous starch particles have shown an excellent safety profile in clinical use. Starch is non irritating and rapidly cleared from the body.

Starch micro particles are described by Ji in U.S. Pat. No. 8,575,132. Ji shows a modified starch material for biocompatible hemostasis, biocompatible adhesion prevention, tissue healing promotion, absorbable surgical wound sealing and tissue bonding, when applied as a biocompatible modified starch to the tissue of animals. The modified starch material produces hemostasis, reduces bleeding of the wound, extravasation of blood and tissue exudation, preserves the wound surface or the wound in relative wetness or dryness, inhibits the growth of bacteria and inflammatory response, minimizes tissue inflammation, and relieves patient pain. Any excess modified starch not involved in hemostatic activity is readily dissolved and rinsed away through saline irrigation during operation. After treatment of surgical wounds, combat wounds, trauma and emergency wounds, the modified starch hemostatic material is rapidly absorbed by the body without the complications associated with gauze and bandage removal. This starch particle may be described as biocompatible modified starch, wherein the biocompatible modified starch is modified by carboxylation or hydroxylation of glucose unit contained in the starch, wherein the biocompatible modified starch exhibits (1) water absorbency capacity of at least 1 times its own weight; (2) a viscosity of a 6.67% suspension not lower than 30 mili Pascals at 37° C., wherein the hemostatic product has an adhesiveness sufficient to form a starch-blood coagulation matrix upon contacting a wound tissue; and, wherein said hemostatic product is degradable by amylase. The Ji modified starch particles may be further described as the hemostatic powder of the present invention is made by an agglomeration process and pellet fabrication. Normally, modified starch grain dimensions are relatively small and light and may need to agglomerate into larger sizes and heavier weights that can readily disperse into the excess blood and generate coagulation close to the broken vessels to achieve an optimal hemostatic outcome. The agglomeration process may not be necessary for large sized modified starch particles such as grafted starch or cross-linked starch. The modified starch particles of Ji have a diameter range of 10 to about 1000 μm, preferably 30 to about 500 μm. Starch particles with diameters of 30 to about 500 μm represent no less than 95% of the total starch particles in the preferred embodiment. The measured, optical diameter of the starch particles is between 50 to about 25 μm.

Specifically, because pre-agglomerated modified starch particles are small and lightweight, they readily form a colloid on the particle surface with the moisture in blood. In this case, it affects the hemostatic outcome by preventing water molecules from further dispersing to other starch particles. The present invention accepts and adopts agglomeration processing technologies in the food and pharmaceutical industries to accumulate microscopic modified starch particles in the general range of 5 to about 50 μm in diameter, creating clinically applicable particles with a diameter range of 30 to about 500 μm. Modified starch particles produced by the process disclosed above exhibit rapid water absorption, strong hydrophilic properties and rapid dispersion in blood to achieve improved hemostatic outcomes, while not readily forming a colloidal protecting layer which may disrupt the hemostatic effect. To fulfill the requirements of clinical operations, the present invention provides various methods and processes to produce hemostatic compositions with acceptable properties that assist doctors with hemostatic therapy during surgery. The powder form modified starch hemostat readily adapts to diffuse oozing of blood on large surface areas, and the hemostatic powder can be delivered to a bleeding wound surface under celioscope, nasoscope, laparoscope or endoscope. The powder will have a sealing effect on postoperative biliary fistulas, thoracic cavity fistulas, lymph fistulas, intestinal fistulas, and wound tissue exudation. Excess residual powder can be rinsed away with normal saline to reduce the risk of inflammation and infection.

This additional coagulant material can be added directly to the modified starch hemostatic sponge or foam of the present invention during the vacuum freeze-drying production process to produce a composite hemostatic sponge or composite hemostatic foam The production process can, but not limited to, pre-mixing the coagulant material with the modified starch directly before vacuum freeze drying process.

The starch agents may be formed by vacuum freeze drying, which is a drying method that freezes wet material or solutions to a solid state under low temperatures (−10 to about 50° C.) and then converts the solid material into a gas and then, in a vacuum (1.3-1.5 Pa), back to a solid material without an intermediate liquid phase (sublimation). As the vacuum freeze drying is processed under low temperature and low pressure, the moisture sublimes directly to produce a substance with numerous special properties.

The basic parameters of the vacuum freeze-drying process specify both physical parameters and process parameters. The physical parameters include thermal conductivity, transfer coefficient, etc. The process parameters include freezing, heating, state of the material, etc. Continued research on this freezing process involves experiments to identify the optimal freezing curve.

Starch particles are further described in U.S. Pat. No. 9,649,482 (Roberts) as a hemostatic agent. They may be used in combination with the collagen materials of the present technology and may include amylopectin, modified pregelatinized potato starch, pregelatinized starches, or modified pregelatinized starches in various forms as a hemostatic agent. Amylopectin particles may be used in various applications as a hemostatic agent. Modified (cross-linked) pregelatinized amylopectin particles may be used as a hemostatic agent. This substance is easily absorbed by the body. It may promote stable clotting because it is a long-branch molecule. It may also promote rapid clotting due to its ability to rapidly absorb water. Particles of other pregelatinized starches or modified pregelatinized starches may also be used as hemostatic agents and may perform better than hemostatic agents that have not been pregelatinized. As was the case above in connection with the sponge, amylopectin, modified pregelatinized amylopectin, pregelatinized starches, or modified pregelatinized polysaccharides may be combined with one another or with other hemostatic agents in particle form (or in other forms as set forth below). Such a mixture could include 50%, 60%, 70%, 80%, 90%, 95% or any other percentage of amylopectin, modified pregelatinized amylopectin, pregelatinized starches or modified pregelatinized starches, with the remainder of the hemostatic powder mixture being particles of another hemostatic agent (or another one of amylopectin, modified pregelatinized amylopectin, pregelatinized starches or modified pregelatinized starches).

Where a particle form of amylopectin, modified pregelatinized amylopectin, amylopectin, modified pregelatinized amylopectin, pregelatinized starches or modified pregelatinized starches is used as a hemostatic agent, particles of a clotting accelerator such as those discussed above may be combined with the hemostatic agent in treating a wound. The same options discussed above in connection with sponge in terms of medications are applicable to the use of these agents in particle form. Particles of the medication could be mixed with the particles of hemostatic agent(s), and/or clotting accelerators.

To make the amylopectin, modified pregelatinized amylopectin, amylopectin, modified pregelatinized amylopectin, pregelatinized starch or modified pregelatinized starch particles, the substance may be dissolved in a solvent and then freeze dried by any suitable freeze-drying technique. In some cases, the amylopectin, modified pregelatinized amylopectin, pregelatinized starch or modified pregelatinized starch may be mixed, in a ratio by weight of 80/20, 70/30, 60/40 or any other ratio, with one another or another hemostatic agent such as amylose. It may also be mixed with multiple hemostatic agents. In some cases, a clotting agent may be dissolved and mixed with the hemostatic agents before freeze drying. The same options regarding shearing and degassing are applicable to the powder form of the hemostatic agent. The resulting particles may have an average diameter of 0.5 μM to 1,000 μM with a preferred mean diameter of 2 μm.

The hemostatic starch particles described by Ji, Drake and Roberts are very efficacious when properly applied. Their rapid removal by tissue and serum amylase activity and the inert nature of starch yield a high degree of safety. However, their powdery nature causes difficulties in application. The rapid reaction of the starch particles with blood requires that, for a successful application, excess blood must be removed before application. Excess blood reacts with the starch particles to form a barrier that prevents the particles from reaching the injured tissue. This barrier can reduce the hemostatic effect of the particles. Conversely, fibrous materials, such as Avitene and other collagen micro fibrils can absorb excess blood and are easier to apply. This ease of application is a significant factor in their successful use as hemostats. The fibers can be easily inserted into complex wound sites and produce a tamponade effect which is augmented by the platelet activating effect of collagen. Since platelet activation requires several minutes to achieve maximal effect the immediate hemostatic effect of collagen fiber application is due to tamponade.

Figure 1:
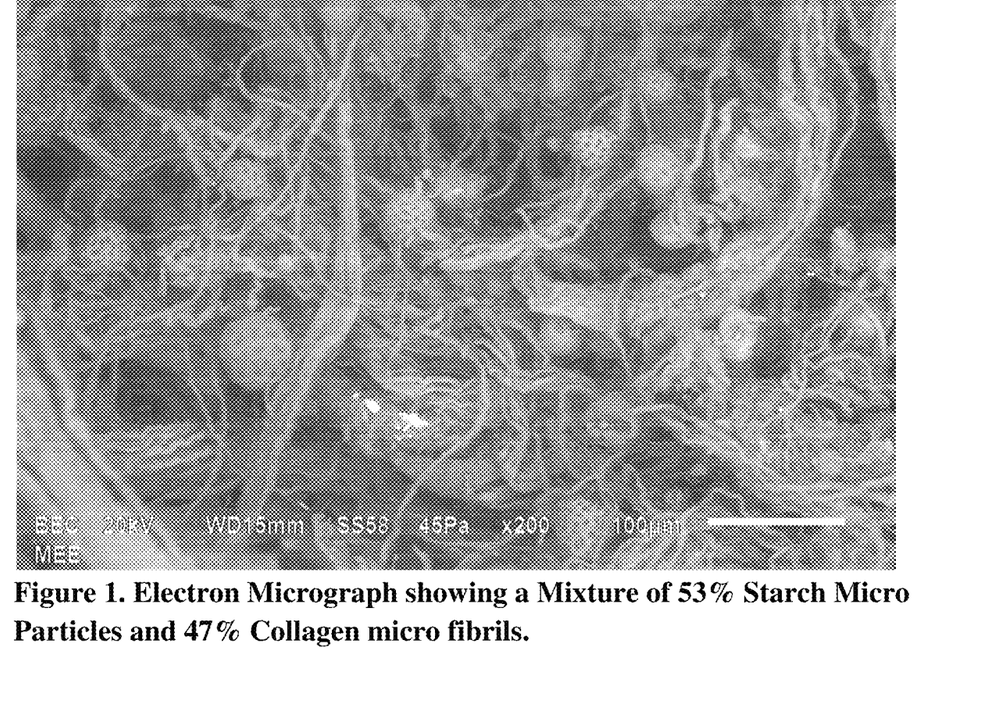
FIG. 1. Electron Micrograph showing a Mixture of 53% Starch Micro Particles (Arista®) and 47% Collagen micro fibrils (Avitene®).
Figure 2:
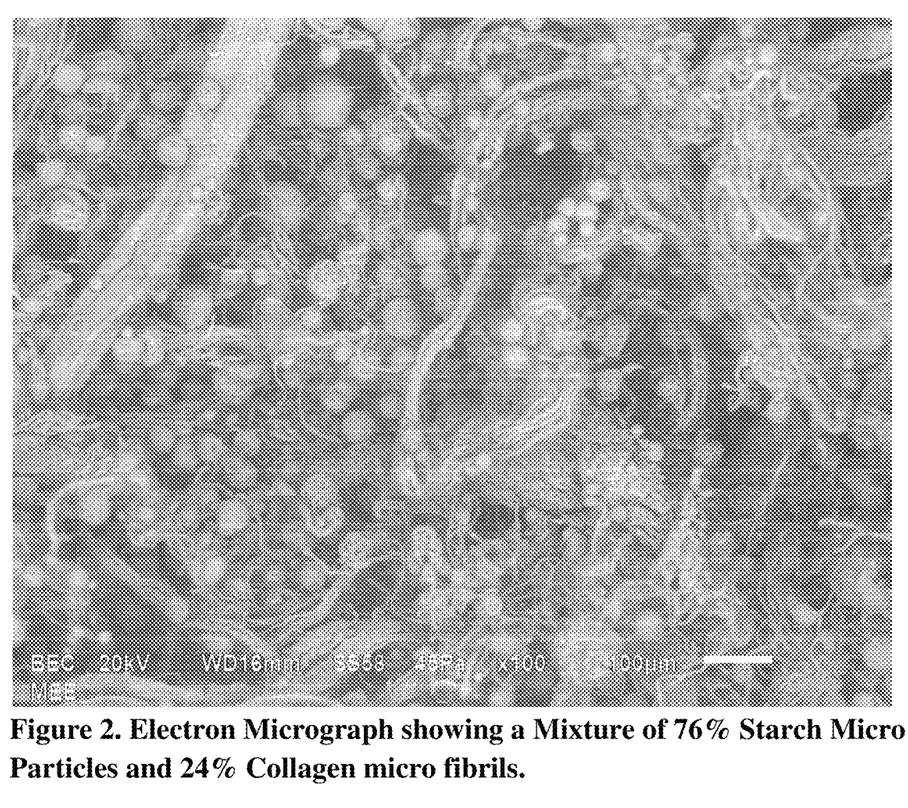
FIG. 2. Electron Micrograph showing a Mixture of 76% Starch Micro Particles (Arista®) and 24% Collagen micro fibrils (Avitene®).

Discovery:

To test the properties of the combination of collagen and starch particles in providing a useful hemostatic combination, a combination of 47% w/w collagen micro fibrils (Avitene®, CR Bard) and 53% w/w starch microparticles (Arista®, CR Bard) was blended, with surprising results. The free-flowing Arista® powder disappeared into the collagen fibrils and the mixture became a fluffy, coherent structure which held together and could be easily manipulated as a unit. The term fluffy means that the powder, fibers and/or mixture is soft and like wool or hr; light and contain a substantial amount of air, up to being filed with air. Fluffy materials (before they are loaded or filled) should have at least 40% by volume of air, preferably at least 50% by volume of air, and even up to 90% and 95%% by volume of air. The entire mass of Avitene®/Arista® could be lifted as a single entity, with extremely little (less than 5%) loss of the microparticles. Before blending, the Avitene® fibrils were loosely cohesive and the Arista® particles 1o were a free-flowing powder. Before blending, grasping Avitene® fibrils with a forceps yielded a small amount of material in and around the forceps jaws, as the fibrils easily separated. Adding an approximately equal amount by weight of Arista® to the Avitene® mass produced a coherent ball. The entire mass (with less than 5% fibril or particle loss from the physical blend of Avitene®/Arista®) could be picked up with the same forceps and manipulated as a unit. A scanning electron micrograph of the resulting mixture is shown in FIG. 1. Loading even larger amounts of Arista® starch particles (76% Arista® and 24% Avitene® collagen particles) produced similar results. FIG. 2 shows a scanning electron micrograph of this mixture. Combinations of Avitene®/Arista® at ratios up to 90% Arista® still produced cohesive composites with minimal loss (less than 5% of total weight) of starch particles when reasonably handled with forceps.

Similar results are seen upon combination of Avitene® with the modified starch particles (Responder® starch particles) described by Ji. Blending 55% Responder® and 45% Avitene® produce a coherent mass with none of the powder-like 2s properties seen in the modified starch particles. The entire mass was a single coherent fibrous mass similar to the original Avitene® fibrils, but with even greater integrity.

The unexpected ability of the collagen fibrils to sequester large amounts of starch micro particles at loadings up to 90% starch by weight provides a new, useful composition of hemostatic agents. This ability to convert free-flowing starch particles into a coherent fibrous mass creates a new hemostatic composition with enhanced efficacy and much improved ease of placement in complex wound sites.

This unusual composition of collagen microfibrils and starch particles presents many useful advantages over either product alone. Collagen fibrils are easy to manipulate and apply to bleeding areas but have limited hemostatic effect. As discussed earlier, much of the efficacy of collagen fiber hemostats, such as Avitene, relies on the tamponade produced by packing the fibers into the bleeding wound. Starch-based hemostats, such as Arista, are free-flowing powders and as such are difficult to handle and apply. Once successfully applied, Arista and other starch-based hemostats show excellent efficacy.

The ability of the collagen fibrils to sequester the free-flowing starch particles into a coherent mass creates a unique and unexpected formulation. The Avitene/Arista mass can be applied in the same manner as Avitene alone. Since the composition can be formed with high loading of the starch particles (75 to 80%), the composite has the ease of handling of the collagen micro fibers and the high efficacy of the starch micro particles. The Avitene/Arista mass can be grasped by forceps or by fingertips and applied easily to complex bleeding sites that would be difficult to reach with powdery Arista alone. Once applied the fibrous mass reacts according to its major constituent, the Arista starch microparticles. Thus we see the the unusual benefit of the composition; the application ease of the collagen micro fibrils combined with the superior hemostatic efficacy of the starch hemostat.

This effect can be seen by the following example.

Example 1. Porcine Bleeding Model

A Yorkshire Cross pig weighing between 45 to 80 kilograms was anesthetized according to an approved protocol developed by American Preclinical Services, Minneapolis Minn., a USDA registered test facility with AAALC accreditation. All procedures followed protocol guidelines.

The liver was exposed using standard surgical procedures. A five millimeter biopsy punch was used to remove a plug of liver tissue approximately 5 to 6 millimeters long. Excess blood removed with gauze followed by immediate application of the test substance. Using a forceps, the test article was inserted into the lesion, covered with a piece of transparent film (Parafilm) and held in place with mild pressure for 30 seconds. Pressure was released and the site was observed for an additional 30 seconds. If no bleeding or oozing of blood was observed, the application was scored as a success. Bleeding or oozing from the wound was scored as a fail.

For the first test, a blend of 75% Arista and 25% Avitene was compared to Avitene only. A total of 26 lesions were made. Thirteen (13) were treated with the 75% Arista/25% Avitene blend. The remaining thirteen were treated with Avitene only. A second test using a blend of 50% Arista/50% Avitene was also made. The results are summarized in Tables 1 and 2.

TABLE 1

Evaluation of hemostatic efficacy in porcine bleeding model. Comparison of 75% Arista/25% Avitene to Avitene only.

| Treatment | Pass | Fail | Totals |
| --- | --- | --- | --- |
| 25% Avitene/75% Arista | 12 | 1 | 13 |
| Avitene Only | 6 | 7 | 13 |
| Totals | 18 | 8 | 26 |

TABLE 2

Evaluation of hemostatic efficacy in porcine bleeding model. Comparison of 50% Arista/50% Avitene to Avitene only.

| Treatment | Pass | Fail | Totals |
| --- | --- | --- | --- |
| 50% Avitene/50% Arista | 5 | 0 | 5 |
| Avitene Only | 6 | 7 | 13 |
| Totals | 11 | 7 | 18 |

An evaluation of these results was performed using software from MedCalc.org. Using Fisher's Exact Test as an indication of a difference between the two groups gives a p value of 0.0030. That is, the two groups are significantly different with respect to efficacy in this model with a probability less than 0.05. Also using the data in Table 1, an estimate of the efficacy of the two compositions can be made. For 25% Avitene/75% Arista we have 12 successes out of a total of 13 for a 92.3% success rate. For Avitene alone we have 6 successes of 13 totals for a 46.2% success rate. A comparison of the difference by MedCalc gives:

Difference(92.3%−46.2%)=46.1% $p=0.0125$

For the 50% Avitene/50% Arista versus Avitene only, Fisher's Test indicates that there is a 10% probability that the result could be due to chance. An estimate of an estimate of the difference in efficacy is:

Difference(100%−46.2)=53.8%.$p=0.0415$

The difference between the success rates of 50% Avitene/50% Arista versus Avitene® only is significant.

The examples demonstrate the advantages of the mixture. Equivalent weights (100 to 150 milligrams) of either Avitene® alone or Avitene®/Arista® (25%75%) were applied to the bleeding wounds. The mixture-controlled bleeding in 92.3%% of the wounds compared to 42.6% using Avitene® alone. This is a highly significant result with a probability of 0.0125 when tested using Fisher's Exact Test. Similar results were seen when the 50% Avitene/50% Arista mixture was applied. The tests show that equivalent amounts of the mixture of Avitene/Arista mixture versus Avitene® alone give superior results when applied to the test wounds.

The composites are surprisingly easy to produce. Simple kneading (with less than 15 pounds/square inch of force, insufficient force to significantly break down the average size of the fibrils by more than 10% in average length) of the mixture of collagen and starch particles results in the disappearance of the starch particles into the collagen fibrils. The mixtures are stable and show no appreciable separation after several months of storage.

Due to the ease with which the composites of this disclosure can be prepared, it is anticipated that for some uses, blending of the two materials at the time of use to produce the herein described composites may be desirable. In other cases, pre-blended packaged composites would be most useful. For ease of use and in order to eliminate the need for physicians to manipulate the product at the time of use, it is anticipated that prefabricated blends of collagen fibrils and starch particles of this disclosure would be most useful. Composites could be prepared with known ratios of collagen micro fibrils and starch particles, packaged in convenient sizes, and sterilized. The preferred method of sterilization is Cobalt (60) gamma irradiation or electron beam irradiation of the final sealed package. Many packaging concepts are available to the medical device industry. Generally devices intended for medical uses are packaged in either a pouch formed of flexible film or in a rigid tray sealed with a flexible lid. A variety of plastics are used for the package. Pouches are formed from Tyvek® film or plastic film multi laminate films. A typical three-layer multi laminate film would consist of heat sealable polyethylene inner and outer layers with a sandwich layer of metalized polyester. Trays are formed from polyethylene terephthalate glycol, polyvinyl chloride, polycarbonate, polypropylene or high impact polystyrene. For use in surgical suites, where a sterile field is established and maintained, packaging is designed with double layers. The outer layer is opened at the edge of the sterile field; the inner package is passed into the sterile area and opened for use. For trauma or treatment of superficial wounds in a non-sterile environment, single layer packaging is satisfactory. In either case, preformed product packaged and ready for use would be desirable. For surgical uses, packages sizes of 0.5 to 5 grams are currently favored. For trauma, larger packages, up to 25 grams, are used. Preformed, ready-to-use, composites would be most useful in both surgical and trauma applications. In surgery, it is desired to minimize the time used to prepare materials. Manipulating and blending fibers and powders at the surgical site uses valuable time and personnel. Surgeons value the speed and ease of use that the composites would provide. In addition, preformed composites can be manufactured in a controlled fashion and through blending and quality controls can be ensured. Many trauma applications present with severe bleeding and require fast action to minimize blood loss. Blood loss is the single largest cause of death following severe trauma. A ready-to-use product would be immediately available to control bleeding.

On the other hand, both the collagen micro fibrils and the starch particles required to form the composites are available to most practitioners as separate items. Collagen micro fibrils are offered by CR Bard (Avitene®) or Ethicon (Instat®) and other manufactures. Starch particles are marketed by CR Bard (Arista) and Starch Medical, Inc. (Responder™ or PerClot™). Extemporaneous preparation of the composites could then be accomplished by mixing the two components and blending thoroughly to attach the starch particles to the collagen fibrils. In the case where the preformed composite was not available, this method could be used to prepare useful composites. There is no inherent reason why composites prepared on site from separate components would fall outside of the scope of this disclosure and not be useful hemostats. Therefore, all composites of the collagen micro fibrils and starch particles prepared according to this disclosure would be expected to be equivalent, regardless of whether they were preformed and packaged as an entity or prepared extemporaneously from the individual components.

The unusual properties seen upon blending the collagen with starch particles can be examined further by considering the properties of the two materials. Some insights, without abandoning other possible explanations, can be gained from closer examination of the mixtures.

Figure 3:
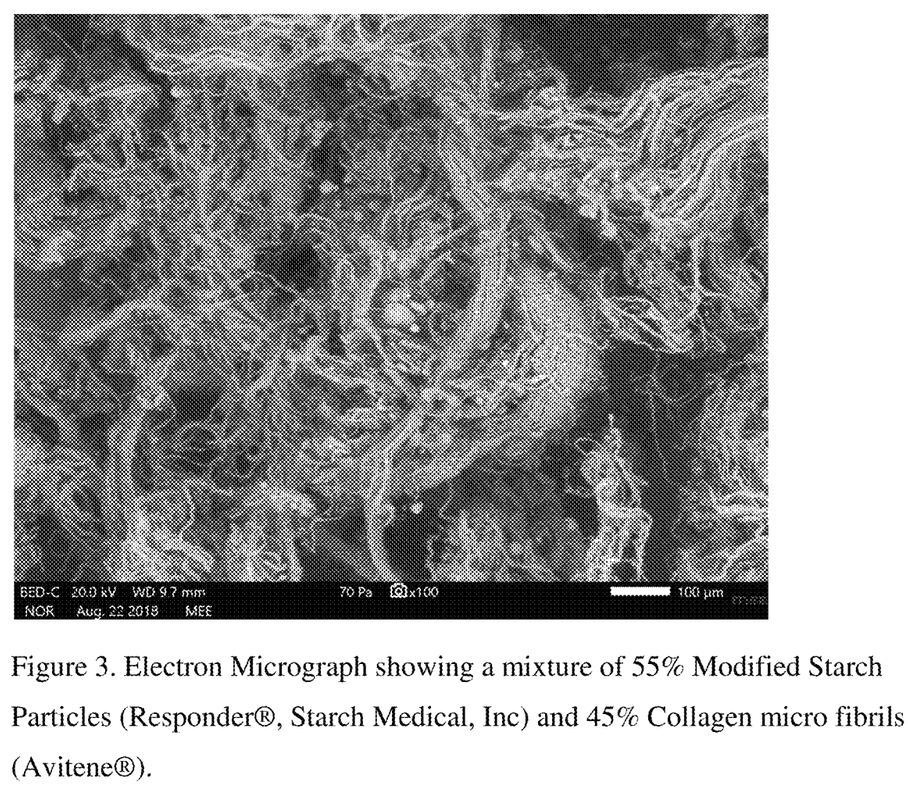
FIG. 3. Electron Micrograph showing a mixture of 55% Modified Starch Particles (Responder®, Starch Medical, Inc) and 45% Collagen micro fibrils (Avitene®).

Microscopic examination of the experimental mixtures shows that both the starch Arista® particles and the modified starch Responder® particles were adhered to the Avitene® collagen fibrils and bridged adjacent collagen fibrils. Scanning electron microscopic images, FIGS. 1-3, of the mixtures show the spherical starch particles adhering to and bridging the collagen fibrils. The attachment is seen to be especially evident where the starch particles contact the smaller fibrils extending from the larger collagen fibrils.

It is believed, without precluding other possibilities, that the initial blending of the two materials, both of which are dry and non-conductive, creates static attraction that initially draws the two materials together. This close attraction then allows strong dispersive forces to act and hold the composite together in a more permanent adhesive bond. Collagen, a protein, contains many polarizing groups due the high content of oxygen and nitrogen atoms. The potential for hydrogen bonding to produce hornification during processing of collagen to produce micro fibrils as described in the Battista Patent is evidence of the potential for collagen to form strong bonds via hydrogen bonding. The high surface area of the fine collagen fibrils exposes these groups at the surface of the fibrils. Starch contains many hydroxyl groups on the sugars that make up the polymer chains. Due to the oxygen-hydrogen bond, these hydroxyl groups are strongly polarized and hydrogen bonding with other polar groups, such as those in the collagen fibrils is favored. The hydroxyl-rich nature of the starch particles surface creates good conditions for dispersive adhesion forces between the two materials. Thus both materials are rich in polarized groups such as hydrogen, oxygen and nitrogen atoms that can form dispersive (Van der Waals) adhesive forces. Coupled with the high surface area of both materials, adhesive bonding occurs once the particles are blended together.

Such hydrogen bonding and other dispersive effects can result in strong surface-to-surface adhesion under the right conditions. Once formed, the cohesive Van der Wals bonds produce a stable mixture in which the starch micro particles are tightly entrapped in the collagen micro fiber matrix. The formation of this stable composite creates a new and useful hemostatic composition.

The utility of the invention is enhanced because of an increased ease of handling of the mixture plus an enhanced hemostatic effect. Starch micro particles, being a free-flowing powder, are difficult to handle and apply. Forming the composite surprising alleviates this, as typical particle applications to a carrier such as gauze, still allows the powder to separate and continues to make handling of the material difficult. The collagen fibrils act to convert the starch particles from a free-flowing powder into a composite, and the starch particles act to conglomerate the loosely adherent collagen fibrils into a composite with better handling properties, all while the composition remains soft and airy, with a density of about 0.04 to 0.50 grams per cubic centimeter.

The unusual nature of the mixtures can be seen from the following experiment in which increasing amounts of Arista starch particles were added to a one gram sample of Avitene contained in a graduated tube. The sample was mixed and the volume noted. The results are shown in Table 3.

TABLE 3

Volume Changes upon mixing Avitene and Arista

| Amount of Avitene, gm | Amount of Arista, gm | Volume, of the mixture, cc | Bulk Density, gm/cc | % Arista |
|---|---|---|---|---|
| 1.03 gm Avitene | 0.0 | 23 | .045 | 0.0 |
| 0.75 gm Avitene | 0.0 | 17 | .044 | 0.0 |
| 1.03 gm Avitene | 0.97 | 22 | .091 | 48.7 |
| 0.75 gm Avitene | 1.11 | 15 | 0.12 | 59.8 |
| 1.03 gm Avitene | 2.83 | 20 | 0.19 | 73.4 |
| 1.03 gm Avitene | 4.00 | 21.5 | 0.23 | 79.6 |
| 1.03 gm Avitene | 8.91 | 25 | 0.40 | 89.7 |
| 0.0 gm Avitene | 9.02 | 12.5 | 0.72 | 100 |

Some additional detail regarding the results seen in Table 2 can be seen from a simple first order approximation of the volume occupied by the collagen fibrils in the Avitene composition. Battista et al (U.S. Pat. No. 3,742,955) states that bulk densities of 1.5 to 6.0 pounds per cubic foot are the preferred range for effective collagen microfibril preparations. The measured bulk density of the Avitene used to prepare the blends shown in Table 2 is 0.045 gm/cc. This corresponds to 2.8 pounds per cubic foot. One cubic centimeter of collagen micro fibrils with a density of 0.045 gm/cc will contain 0.045 grams of collagen. Since high molecular weight proteins, like collagen, have crystalline densities of approximately 1.4 grams/cc (Fisher, et al, Protein Science (2004) 13: 2825-2828), the actual space occupied by the collagen in one cubic centimeter of collagen micro fibrils is 0.045 gms/1.4 grams/cc=0.032 cc. The remaining space in the one cubic centimeter bulk volume is void volume or 1-.032=0.97 cc. Thus we see that approximately 97% of the space in a collection of collagen microfibrils is empty space. This space can be filled with starch microparticles as the composites are prepared. A simple test for coherence of the composition of the present technology is to pick up a 0.1 gram clump of the composition with household tweezers, using no more than 150 g/cm$^2$ of pressure against the composite by the ends of the tweezers. Moving the composite sample and depositing it onto filter paper, and weighing the sample after movement to see if less than 5% of the total weight of the combined starch and collagen has been lost in the transmittal. If the sample has lost less than that 5% of the total weight of starch particles, the composition is deemed coherent.

Methods of forming starch particles into structures such as sheets require an additive to adhere the particles together. A simple wetting of the starch particles, forming into sheets and drying is not successful since the dried sheets are brittle and have poor strength. Both water and polar solvent-based adhesives coated the particles and reduced their efficacy. Water based adhesives also cause the particles to collapse upon drying unless the water is removed by lyophilization. Collagen fibrils can be formed into sheets or foams as described by Maddalo, et al in U.S. Pat. No. 6,454,787. by freeze drying slurries of collagen fibrils. Similarly, freeze drying a mixture of collagen fibrils and starch particles can be used to form composite sheets of collagen and starch micro particles since the collagen fibrils connect the starch particles in a stable form. Making a composite by blending small amounts of (2 to 10%) Avitene® collagen particles with Arista® or Responder™ starch particles in water and freeze drying yields composites with good integrity. Using small amounts of Avitene® fibrils as a binder for larger amounts of Arista® gives sheets that are useful hemostats where application of powder is difficult.

Sourcing and preparing collagen into micro fibrils is expensive. Avitene® collagen particles sell for over $200 per gram. Arista® starch particles are available for around $30 per gram. Small amounts of Avitene® can incorporate larger amounts of Arista® (up to 80% Arista® by weight) to produce a unique hemostatic composite with superior handling and hemostatic properties.

The hemostatic plug formed by applying the mixtures described herein to bleeding wounds is expected to have advantages over the use of either material alone. Collagen micro fibrils alone provide a strong clot due to the reinforcing nature of the fibers, but adherence to tissue is weak. Starch particles produce a tenacious clot due to the thick gel of serum proteins and blood cells, but the actual clot is thin and rather weak. The combination of fibers for increased strength and starch particles for strong adhesion yields the expected synergistic effect along with the unexpected advantage of superior handling of the mixture.

Collagen persists in tissue for several weeks but starch microparticles are degraded and removed from tissue within 24 to 48 hours. This difference in absorption rates will create an unusual and, most likely, salutary wound healing environment at the site of application. The initial mix of collagen fibrils and starch micro particles imbedded in a dense clot of fibrin, platelets, and red blood cells will quickly convert into a porous Swiss cheese-like matrix due to the rapid removal of the starch particles by serum amylase activity.

Wound healing is a complex process. See for instance *Wound Repair and regeneration: Mechanisms, signaling and translation. Sci. Translation Med.* (2014) 6 (265). The early stages of wound healing are initiated by many of the same hemostatic mechanisms that provide initial bleeding control. Enzymes necessary for removal of fibrin and tissue debris are incorporated into the fibrin network and thrombin used to initiate coagulation also activates key processes required for wound healing, therefore the initial coagulation event sets the stage for subsequent healing processes. In addition, the fibrin network at the injury site provides the scaffold for the migration of keratinocytes and inflammatory cells involved in the early stages of wound repair. This accumulation of keratinocytes, inflammatory cells and fibroblasts at the wound site relies upon the fibrin-collagen clot at the wound site to attract and orient the incoming cells. Forming a porous open structure by incorporating high amount of rapidly degraded starch particles into the fibrin-collagen clot matrix could have beneficial results to subsequent wound healing processes.

The invention claimed is:

1. A method of forming a coherent and stable fluffy powder composition of matter comprising a dry powder blend of collagen fibrils adhered to starch particles as a fluffy mass with at least 40% by volume of air with hemostatic properties by physically admixing the collagen fibrils and the starch particles together in a weight ratio of from 2% to 95% of the collagen fibrils and from 98% to 5% of the starch particles based on a total weight of the fluffy power composition, conditioning the blend of collagen fibrils and starch particles to contain 8% to 15% volatiles selected from the group consisting of water and organic liquid for 8 to 24 hours, drying the conditioned blend, and then deaggregating the dried conditioned blend, the fluffy powder composition exhibiting a level of coherence wherein the fluffy powder composition can be lifted, without crushing the collagen fibrils and without loss of more than 10% by a total weight of the starch particles.

2. The method of claim 1 wherein the collagen fibrils have an average length of less than 1000 µm.

3. The method of claim 1 wherein the starch particles have an average diameter of less than 1000 µm.

4. The method of claim 2 wherein the starch particles have an average diameter of less than 1000 µm.

5. The method of claim 1 wherein the coherent and stable fluffy powder composition consists essentially of collagen fibrils and starch particles.

6. The method of claim 1 wherein the coherent and stable fluffy powder composition consists essentially of collagen fibrils and starch particles and less than 10% by weight of an adhesive based on the total weight of the composition.

7. The method of claim 1 wherein the coherent and stable fluffy powder composition consists essentially of collagen fibrils and starch particles and less than 3% by weight of an adhesive based on a total weight of the composition.

8. The method of claim 1 wherein the stable fluffy powder composition has at least 90% by volume of air.

9. The method of claim 1 wherein the stable fluffy powder composition contains 0% binder in addition to the starch and chitosan.

\* \* \* \* \*